(12) United States Patent
Nakao et al.

(10) Patent No.: US 10,352,879 B2
(45) Date of Patent: Jul. 16, 2019

(54) X-RAY INSPECTION METHOD AND DEVICE

(71) Applicant: HITACHI HIGH-TECHNOLOGIES CORPORATION, Tokyo (JP)

(72) Inventors: Toshiyuki Nakao, Tokyo (JP); Yuta Urano, Tokyo (JP); Kaifeng Zhang, Tokyo (JP); Hideaki Sasazawa, Tokyo (JP)

(73) Assignee: HITACHI HIGH-TECHNOLOGIES CORPORAITON, Tokyo (JP)

( * ) Notice: Subject to any disclaimer, the term of this patent is extended or adjusted under 35 U.S.C. 154(b) by 254 days.

(21) Appl. No.: 15/529,874

(22) PCT Filed: Dec. 16, 2015

(86) PCT No.: PCT/JP2015/085155
§ 371 (c)(1),
(2) Date: May 25, 2017

(87) PCT Pub. No.: WO2016/098795
PCT Pub. Date: Jun. 23, 2016

(65) Prior Publication Data
US 2017/0261441 A1    Sep. 14, 2017

(30) Foreign Application Priority Data
Dec. 19, 2014    (JP) .................................. 2014-257691

(51) Int. Cl.
*G01N 23/04* (2018.01)
*G01N 23/18* (2018.01)
(Continued)

(52) U.S. Cl.
CPC ........... *G01N 23/04* (2013.01); *G01N 23/044* (2018.02); *G01N 23/083* (2013.01); *G01N 23/18* (2013.01);
(Continued)

(58) Field of Classification Search
None
See application file for complete search history.

(56) References Cited

U.S. PATENT DOCUMENTS 8,391,581 B2 * 3/2013 Masuda ............... G01N 23/046
378/58
8,644,450 B2 * 2/2014 Kita ..................... G01N 23/223
378/44
(Continued)

FOREIGN PATENT DOCUMENTS

JP    2009-085923 A    4/2009
JP    2009-174972 A    8/2009
(Continued)

OTHER PUBLICATIONS

International Search Report, dated Mar. 15, 2016, which issued during the prosecution of International Application No. PCT/JP2015/085155, which corresponds to the present application.
(Continued)

*Primary Examiner* — Hoon K Song
(74) *Attorney, Agent, or Firm* — Baker Botts L.L.P.

(57) ABSTRACT

A method including inspecting, using an X-ray transmission image, internal defects in a TSV formed in a semiconductor wafer, and detecting the X-rays, and processing an X-ray transmission image. Therein, the detection of X-rays is configured such that: the detection azimuth of the X-rays, and the detection elevation angle of the X-rays relative to the X-ray source are determined on the basis of information on the arrangement interval, depth, and planar shape of structures formed in the sample. The angle of rotation of a rotating stage on which the sample is mounted is adjusted in accordance with the detection azimuth which has been determined, and the X-rays that have been transmitted through the sample are detected with the position of the detector set to the detection elevation angle which has been determined.

15 Claims, 14 Drawing Sheets

(51) Int. Cl.
    *G01N 23/083*     (2018.01)
    *G01N 23/044*     (2018.01)

(52) U.S. Cl.
    CPC ............ *G01N 2223/3306* (2013.01); *G01N 2223/401* (2013.01); *G01N 2223/408* (2013.01); *G01N 2223/6116* (2013.01); *G01N 2223/646* (2013.01); *G01N 2223/6462* (2013.01)

(56) References Cited

U.S. PATENT DOCUMENTS

| | | |
|---|---|---|
| 2003/0095631 A1 | 5/2003 | Rosner |
| 2004/0125909 A1* | 7/2004 | Griffith .................. A61B 6/025 378/4 |
| 2015/0204802 A1* | 7/2015 | Pois ..................... G01N 23/201 378/86 |

FOREIGN PATENT DOCUMENTS

| | | |
|---|---|---|
| JP | 2013-130392 A | 7/2013 |
| KR | 10-2010-0101642 A | 9/2010 |
| KR | 10-2013-0019030 A | 2/2013 |

OTHER PUBLICATIONS

Notification of Reason for Refusal, dated Jul. 5, 2018, which issued during the prosecution of Korean Patent Application No. 10-2017-7010165, which corresponds to the present application (English translation attached).

* cited by examiner

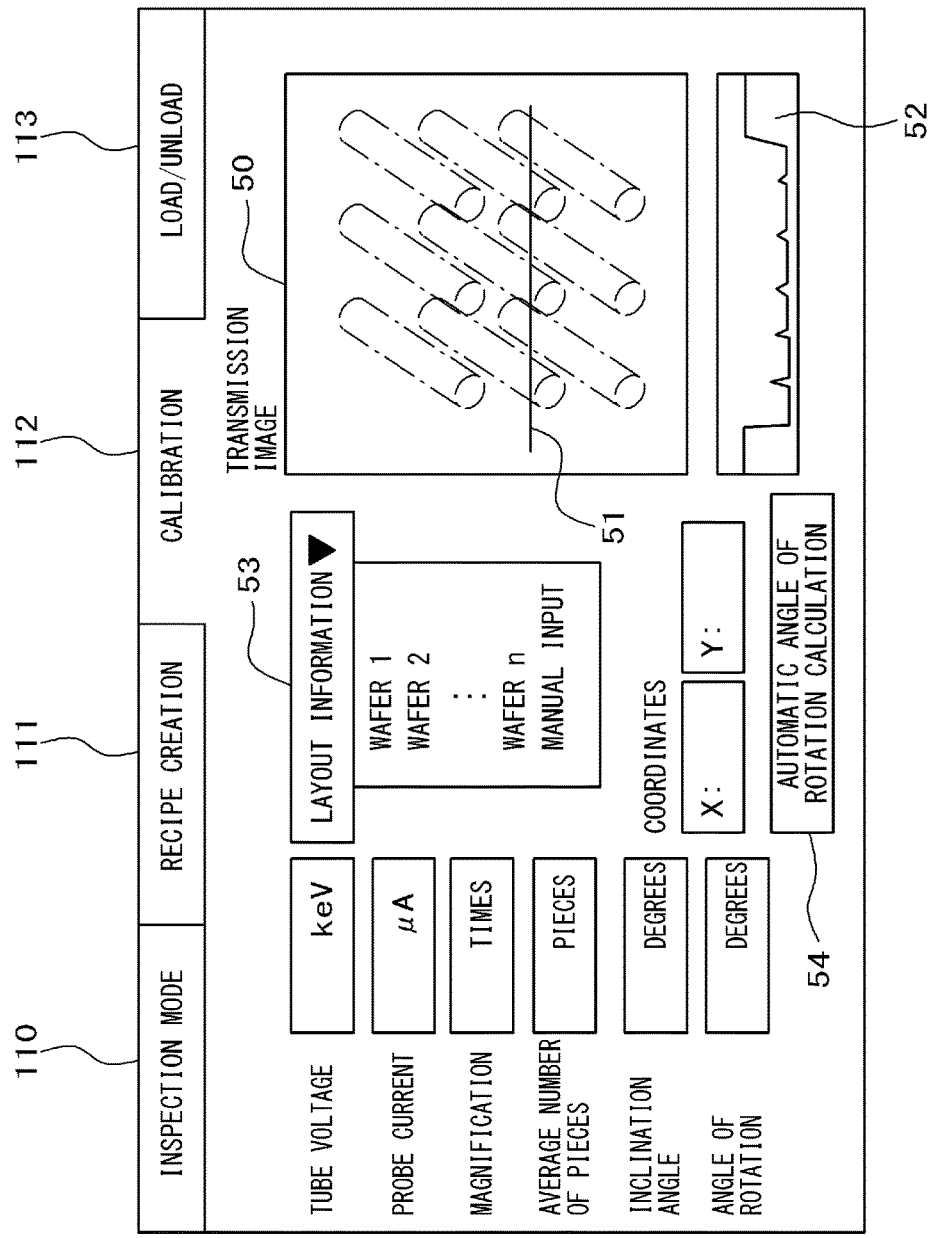

X-RAY INSPECTION METHOD AND DEVICE

CROSS REFERENCE TO PRIOR APPLICATIONS

This application is a U.S. National Phase application under 35 U.S.C. § 371 of International Application No. PCT/JP2015/085155, filed on Dec. 16, 2015, which claims benefit of priority to Japanese Application No. 2014-257691, filed on Dec. 19, 2014. The International Application was published in Japanese on Jun. 23, 2016 as WO 2016/098795 A1 under PCT Article 21(2). The contents of the above applications are hereby incorporated by reference.

TECHNICAL FIELD

The present invention relates to a semiconductor inspection device and method.

BACKGROUND ART

The packing densities of semiconductors have been increasingly made larger and in recent years, 3D multilayering technologies have remarkably evolved. In particular, the TSV (Through Si Via) technologies are expected as the next generation's semiconductor multilayering technologies. The dimensions of each TSV are 20 μm in diameter and approximately 80 μm in depth and TSVs. are minute and high in aspect ratio as compared with microbumps now in wide use in 3D lamination. For this reason, a void that may be produced when TSVs. are formed by Cu plating is prone to be a critical defect and there are the high needs for inspection for voids in TSV. In one of void detection technologies in wide use, an X-ray is applied to a semiconductor wafer (hereafter, referred to as wafer) and an analysis is made on a resulting transmission image and Patent Literature 1 describes a technology in which a wafer surface is irradiated with an X-ray from a direction inclined from the perpendicular direction to detect any void.

CITATION LIST

Patent Literature

PTL: Japanese Patent Application Laid-Open No. 2013-130392

SUMMARY OF INVENTION

Technical Problem

TSVs are high in aspect ratio and regularly arranged. Therefore, when an X-ray transmission image is acquired at an inclined angle, the transmission images of adjacent TSVs overlap with each other and the void detection performance can be degraded. Patent Literature 1 describes a technology in which an object is inclined 45 degrees (elevation angle direction) and transmission images are acquired from at least six directions (azimuth direction). However, since a plurality of TSVs are formed with a narrow pitch, it will be very difficult to avoid overlapping of transmission images if an irradiation azimuth is arbitrarily selected without a selection criterion.

The present invention provides an X-ray inspection method and a device therefor in which the above problem is solved and an X-ray transmission image with overlapping of a plurality of TSVs avoided can be acquired even from a sample (wafer) including the TSVs formed with a narrow pitch and any void, one of TSV detects, can be detected with accuracy at high speed.

Solution to Problem

To address the above-mentioned problem, the present invention provides an X-ray inspection method in which: an X-ray emitted from an X-ray source is applied to a sample to be inspected placed on a rotating stage and having structures formed therein; an X-ray transmitted through the sample irradiated with the X-ray is detected with an X-ray detector; a signal obtained by detecting the X-ray transmitted through the sample, detected with the X-ray detector is processed to form an X-ray transmission image at an image processing unit; and the X-ray transmission image formed at the image processing unit is processed at a defect determination unit to detect any defect in the sample. In this method, the X-ray transmitted through the sample is detected with the X-ray detector by: determining a detection azimuth relative to the sample of the X-ray transmitted through the sample detected with the X-ray detector and a detection elevation angle relative to the X-ray source based on information on the arrangement interval, depth, and planar shape of structures formed in the sample; adjusting an angle of rotation of a rotating stage on which the sample is placed in accordance with the determined detection azimuth; and setting the position of the detector to the determined detection elevation angle to detect the X-ray transmitted through the sample.

To address the above-mentioned problem, the present invention provides an X-ray inspection method in which: an X-ray emitted from an X-ray source is applied to a sample to be inspected placed on a rotating stage and having structures formed therein; an X-ray transmitted through the sample irradiated with the X-ray is detected with an X-ray detector; a signal obtained by detecting the X-ray transmitted through the sample, detected with the X-ray detector is processed to form an X-ray transmission image at an image processing unit; and the X-ray transmission image formed at the image processing unit is processed at a defect determination unit to detect any defect in the sample. In this method, the X-ray transmission image formed by processing a signal obtained by detecting the X-ray transmitted through the sample, detected with the X-ray detector at the image processing unit is displayed on a screen; and on the screen with the X-ray transmission image displayed, a detection azimuth relative to the sample of the X-ray transmitted through the sample, detected with the X-ray detector and a detection elevation angle relative to the X-ray source are determined such that overlapping of the X-ray transmission images of structures formed in the sample is not produced or such that overlapping of the X-ray transmission images of the structures is minimized.

Further, to address the above-mentioned problem, the present invention provides an X-ray inspection device including: a rotating stage on which a sample is placed and which is rotatable within a plane; an X-ray source applying an X-ray to the sample placed on the rotating stage; an X-ray detector detecting the X-ray emitted from the X-ray source and transmitted through the sample; a pivoting stage for adjusting an elevation angle of the X-ray detector relative to a position at which the X-ray source emits the X-ray; an image processing unit processing a signal obtained by detecting the X-ray transmitted through the sample, detected with the X-ray detector to form an X-ray transmission image; a defect determination unit processing the X-ray transmission image formed at the image processing unit to detect any defect in the sample; and a control unit controlling the rotating stage and the pivoting stage. In this X-ray inspection device, the control unit controls an angle of rotation of the rotating stage on which the sample is placed based on information on the arrangement interval, depth, and planar shape of structures formed in the sample or an X-ray transmission image formed at the image processing unit and thereby sets a detection azimuth of the X-ray detector relative to the sample and controls an pivoting angle of the pivoting stage relative to a position at which the X-ray source emits the X-ray and thereby sets a detection elevation angle of the X-ray detector relative to the X-ray source.

Advantageous Effects of Invention

According to one aspect of the present invention, even from a sample (wafer) with a plurality of TSVs formed with a narrow pitch, an X-ray transmission image with overlapping of the TSVs avoided can be obtained and any void, a defect, in TSVs can be detected with accuracy at high speed.

BRIEF DESCRIPTION OF DRAWINGS

FIG. 9 illustrates an example of GUI in Example 1 of the present invention.

SOLUTION TO PROBLEM

The present invention is implemented by: applying an X-ray to an area with TSVs formed therein of a wafer as a sample to be inspected at an angle inclined from the direction perpendicular to the surface of the wafer; at the same time, calculating an X-ray irradiation direction in which the transmission images of adjacent TSVs do not overlap with each other based on geometrical information including the diameter, depth, pitch, and the like of the TSVs; rotating the wafer in an in-plane direction by the above angle; picking up an image of the sample such that adjacent TSV transmission images do not overlap with each other and detecting any defect from this image; or picking up transmission images at an inclination angle at which adjacent TSV transmission images do not overlap with each other and detecting any defect.

The present invention is implemented by: when adjacent TSV transmission images inevitably overlap with each other, calculating the area of an overlap from the brightness information of a picked-up image; rotating the wafer in an in-plane direction so as to minimize overlapping of transmission images and acquiring transmission images; and detecting any defect.

The present invention is implemented by: when there is no layout information of a wafer, carrying out a trial inspection; extracting geometrical information including the diameter, depth, pitch, and the like of TSVs from the acquired TSV image; calculating an angle of rotation of the wafer based on these pieces of information; and detecting any defect.

Hereafter, a description will be given to embodiments of the present invention with reference to the drawings.

Example 1

Figure 1A:
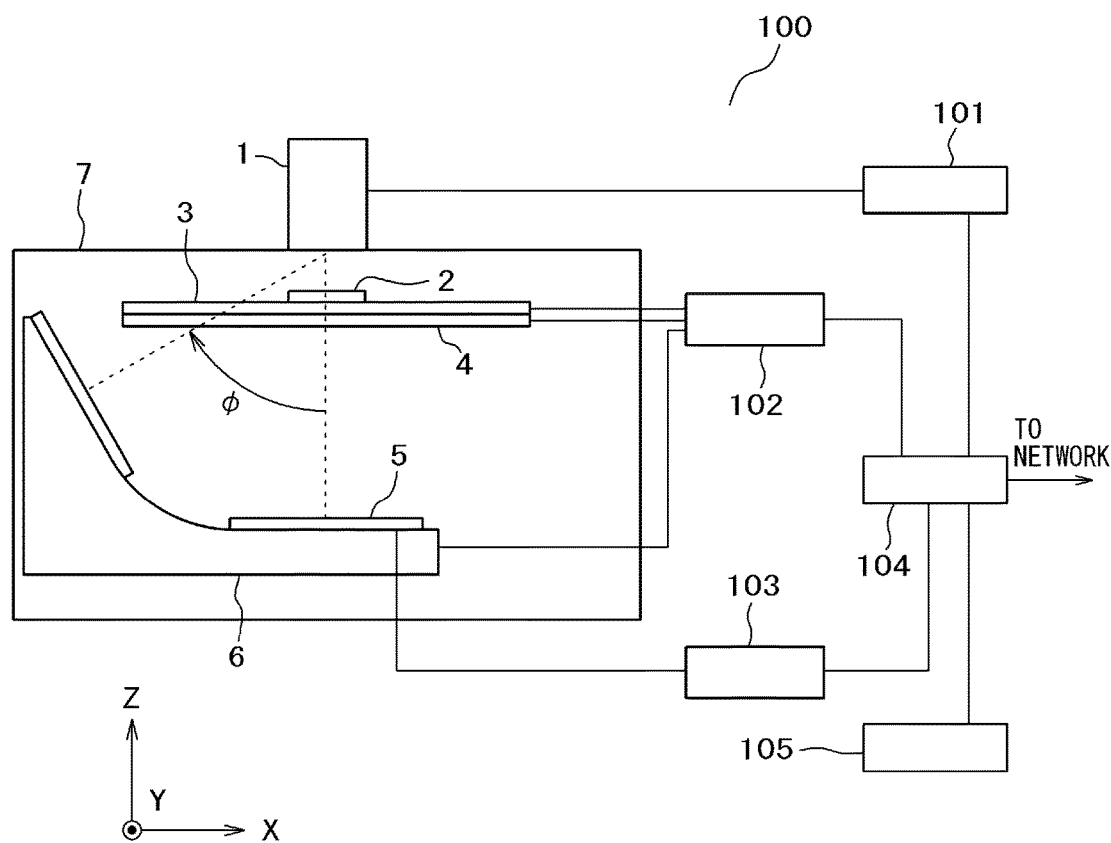
FIG. 1A is a schematic block diagram of an X-ray inspection device of the present invention.

FIG. 1A is a schematic diagram of an X-ray inspection device 100. The X-ray inspection device 100 includes: an X-ray source 1; a translating stage 3 and a rotating stage 4 for holding and moving a wafer 2 to be measured; an X-ray detector 5; a pivoting stage 6; an X-ray shielding wall 7; an X-ray source controller 101; a stage controller 102; an X-ray detector controller 103; a control unit 104; and an input/output unit 105.

The X-ray source 1 comprises an electron optical system and a target (not shown). The electron optical system is a Schottky electron gun and the target comprises a tungsten thin film and a diamond thin film. The translating stage 3 is movable in the X-axis, Y-axis, and Z-axis directions and the rotating stage 4 is rotatable in an XY-plane. (Hereafter, the direction of rotation in the XY-plane of the rotating stage will be defined as θ direction.) The central parts of the translating stage 3 and the rotating stage 4 are made of glass (not shown) low in X-ray absorption.

The X-ray detector 5 is disposed opposite to the X-ray source 1 with the translating stage 3 and the rotating stage 4 in between. For the X-ray detector 5, an image intensifier obtained by combining a scintillator, a fluorescent material, and CCD is used.

An X-ray emitted from the X-ray source 1 is absorbed to a wafer 2 placed on the translating stage 3 and a resulting transmitted X-ray is detected at the X-ray detector 5. The distance between the X-ray detector 5 and the X-ray source 1 is fixed and a magnification and a broadness of coverage are varied by changing the position of the wafer 2 with the translating stage 3. The X-ray detector 5 is rotatable in an XY-plane by the pivoting stage 6 with the X-ray generation position of the X-ray source 1 at the center. (The direction of rotation in the XY-plane will be defined as φ direction.) The wafer 2 is translated with the translating stage 3 in correspondence with this angle of rotation to prevent a measuring area from being brought out of place.

The X-ray source 1, translating stage 3, rotating stage 4, and X-ray detector 5 are placed inside the X-ray shielding wall 6 to prevent leakage of an X-ray to the outside.

The X-ray source controller 101 controls various parameters (tube voltage, tube current, applied magnetic field and applied voltage to the electron optical system, atmospheric pressure, etc.) of the X-ray source 1 and turn-ON/OFF of X-ray generation; the stage controller 102 controls the movement coordinates of the translating stage 3 and the rotating stage 4; and the X-ray detector controller 103 reads data from the X-ray detector 5 and sets imaging conditions (sensitivity, number of pieces to be averaged, etc.).

The X-ray source controller 101, stage controller 102, and X-ray detector controller 103 are controlled by the control unit 104. While the wafer 2 is moved based on inspection conditions inputted to the control unit 104 through GUI in advance, X-ray transmission images are obtained. Such a defect as a void is determined based on the acquired transmission images and an inspection result is displayed on the input/output unit 105.

Figure 1B:
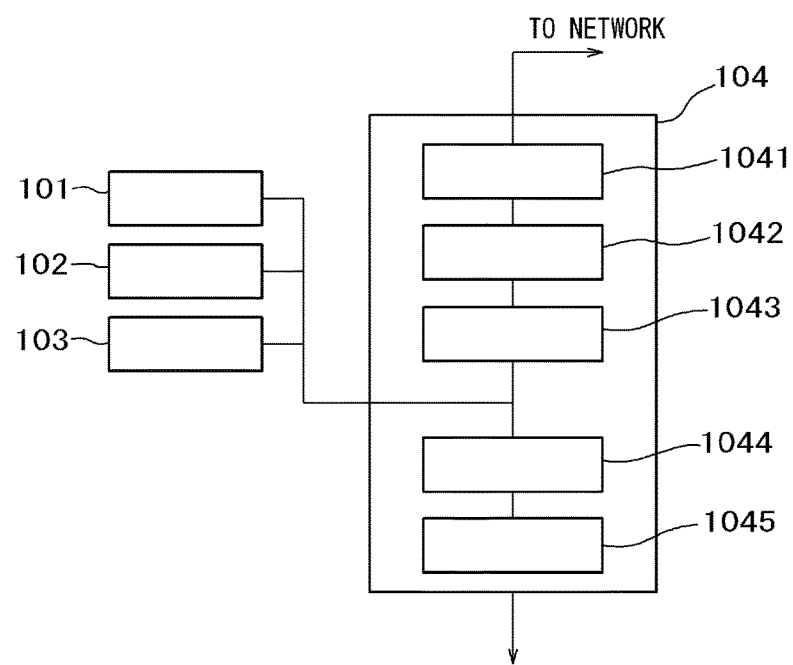
FIG. 1B is a block diagram illustrating a configuration of a control unit of an X-ray inspection device of the present invention.

FIG. 1B illustrates a configuration of the control unit 104. The control unit 104 includes a wafer information input part 1041, an inputted information take-in part 1042, a θ calculation part 1403, an image processing part 1044, and a defect determination part 1045.

The wafer information input part 1041 is for inputting the design information of a wafer to be inspected through a network. The inputted information take-in part 1042 takes in information required to calculate a θ-direction, which is a direction of rotation in a XY-plane of the rotating stage, from among the design information of the wafer to be inspected acquired at the wafer information input part 1041 through the network. The θ calculation part 1403 calculates a θ-direction, which is a direction of rotation in a XY-plane of the rotating stage using the information taken into the inputted information take-in part 1042 from among the design information of the wafer to be inspected. Based on the angle of rotation in the θ-direction calculated at the θ calculation part 1403, the stage controller 102 controls an angle of rotation of the θ stage 4. The image processing part 1044 receives a detection signal from the X-ray transmitted through the wafer 2, detected at the X-ray detector 5 through the X-ray detector controller 103. Further, the image processing part receives control signals for the translating stage 3 and the rotating stage 4 from the stage controller 102 and generates an X-ray transmission image of the wafer 2. The determination part 1045 determines any defect using: information on the X-ray transmission image of the wafer 2 generated at the image processing part 1044; information on the direction of rotation θ in the XY-plane of the rotating stage calculated at the θ calculation part 1403; output information of the X-ray controller 101; output information of the stage controller 102; and output information of the X-ray detector controller 103.

Figure 2:
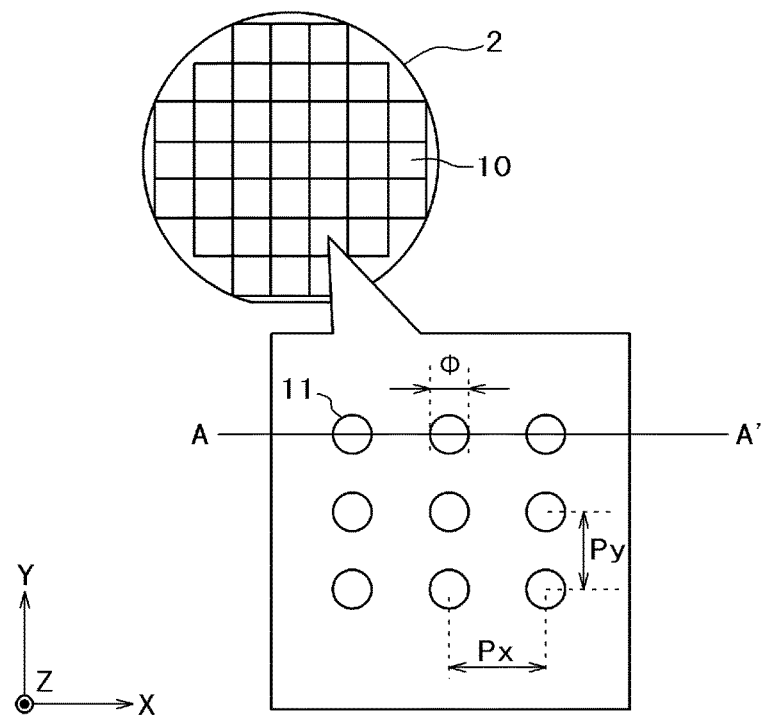
FIG. 2 is a plan view of a wafer.
Figure 3:
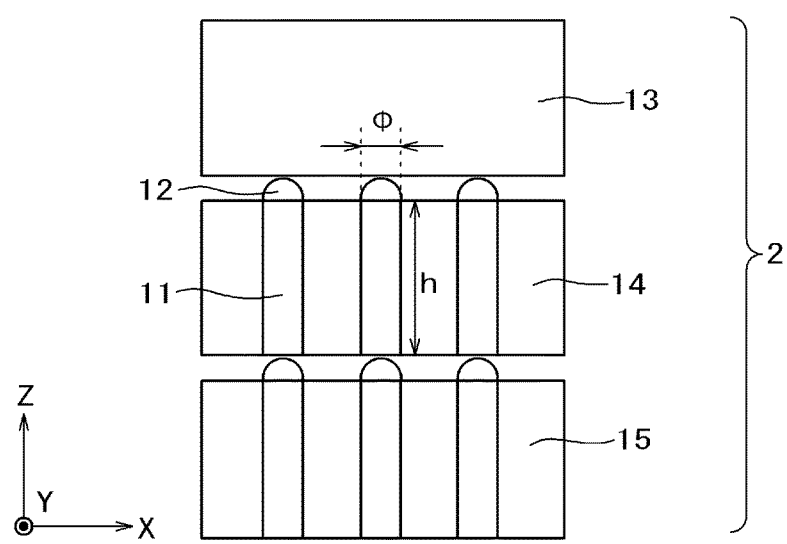
FIG. 3 is a sectional view of wafer.

FIG. 2 and FIG. 3 show examples of schematic diagrams of a wafer 2. FIG. 2 shows a plan view of the entire wafer 2 and a partial enlarged view of an area with TSVs formed therein and FIG. 3 shows a sectional view taken along line A-A' of FIG. 2. A plurality of dies 10 are formed in the wafer 2 and TSVs 11 are formed in some of the dies 10. The TSVs 11 are Φ in diameter and formed with a pitch of $P_x$ in the X-axis direction and with a pitch of $P_y$ in the Y-axis direction. In FIG. 3, a first layer 13, a second layer 14, and a third layer 15 are laminated and these layers are connected together through TSVs 11 and microbumps 12. The length of each TSV 11 is h.

Figure 4:
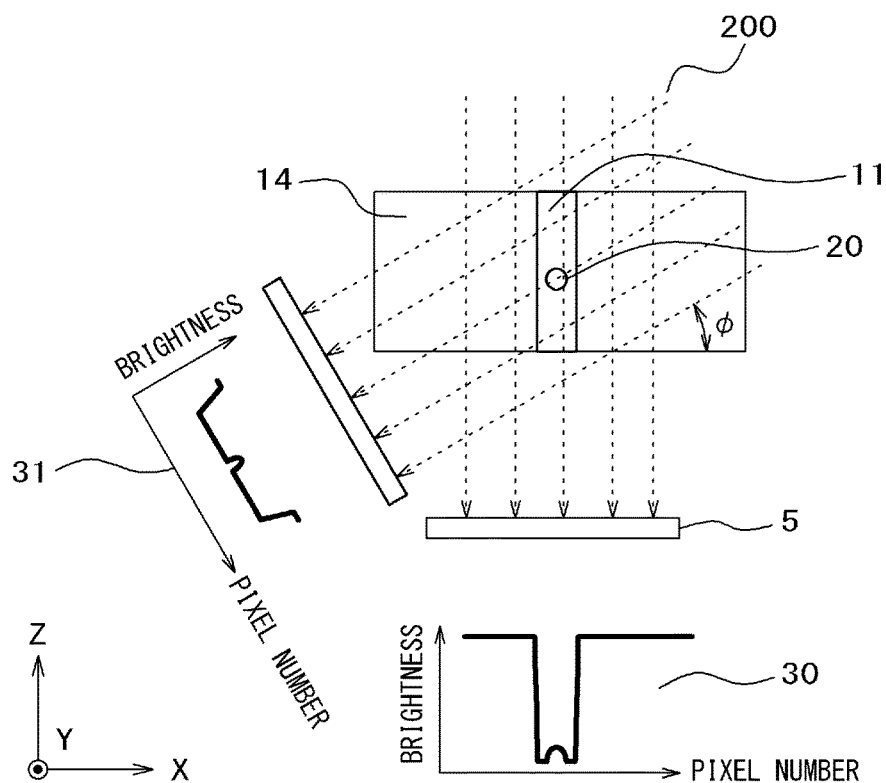
FIG. 4 is an explanatory diagram of an X-ray transmission image obtained when an X-ray is obliquely applied to a wafer.
Figure 5:
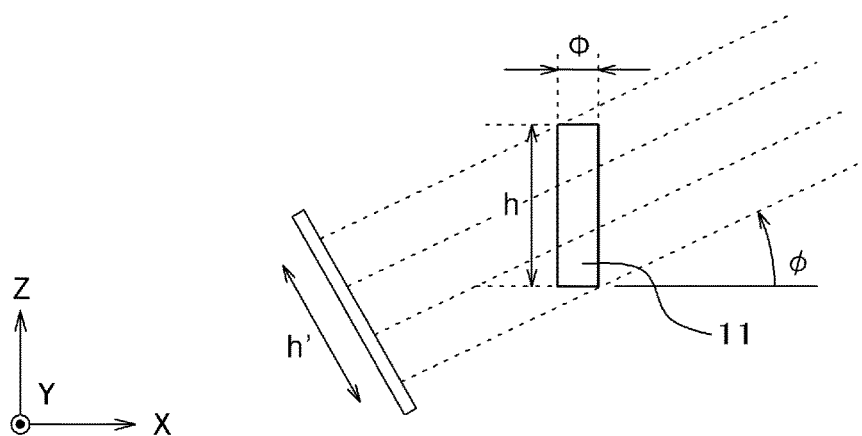
FIG. 5 is an explanatory diagram illustrating a length of a TSV image in an X-ray transmission image obtained when an X-ray is obliquely applied to a wafer.

With reference to FIG. 4 and FIG. 5, a description will be given to a case where the position of the X-ray detector 5 is inclined in the φ-direction in an XZ-plane by the pivoting stage 6 with the X-ray generation position of the X-ray source 1 at the center and an X-ray transmission image of a wafer 2 is acquired. The following description will be given based on an XZ sectional view in which only one TSV 11 formed in the second layer 14 of the wafer 2 is taken out.

TSVs are formed mainly of Cu and Cu has a larger atomic number than Si constituting a major part of the wafer 2 and thus high in X-ray absorption. That is, when an X-ray 200 is applied to the second layer 14 and a transmitted X-ray is detected with the X-ray detector 5, a phenomenon takes place in a picked-up image. An area where a TSV 11 is not present is low in X-ray absorption and thus bright and an area where a TSV 11 is present is high in X-ray absorption and thus dark. Further, if any void 20 is present in a TSV 11, the void area is low in X-ray absorption and only the void area is brighter than the surrounding areas; therefore, the void can be detected through this difference in brightness.

When an X-ray 200 is applied at φ=0 degrees, that is, from the perpendicular direction of the second layer 14, the number of pixels of the X-ray detector 5 detecting the X-ray transmitted through the TSV 11 area is reduced and at the same time, absorption of the X-ray incident upon these pixels to the TSVs 11 is maximized. As a result, like the profile 30 obtained by plotting the brightness (magnitude of output signal) for each pixel number of the X-ray detector 5, the output signal 301 is weakened from a pixel in a position corresponding to the TSV presence area and the brightness of the image becomes very dark. (The pixel number refers to a number assigned when a plurality of linearly arranged pixels of the X-ray detector 5 are sequentially counted from one end.)

When a void 20 is also present in a TSV 11, absorption at the TSV 11 is essentially very high; therefore, the contrast between a detection signal 302 from the TSV 11 and a detection signal 303 from the void 20 is poor and the void 20 detection performance achieved when a detection image is processed is degraded.

Meanwhile, when the X-ray detector 5 is inclined (for example, φ=60 degrees) by the pivoting stage 6 in the φ direction and an X-ray is applied, the number of pixels of the X-ray detector 5 detecting the X-ray transmitted through the TSV 11 area is increased. At the same time, absorption of the X-ray incident upon the pixels at the TSV 11 is reduced as compared with the case where φ=0 degrees. As a result, like the profile 31, among the output signals 311 from pixels in a position corresponding to the TSV presence area, the levels of brightness (magnitude of output signal) of detection signals 312 from the TSV 11 and detection signals 313 from the void 20 are increased and the void 20 can be detected with a higher contrast.

As mentioned above, by inclining the X-ray detector 5 in the φ direction relative to the wafer 2 to acquire X-ray transmission images, the brightness contrast between images of a TSV area and images of a void portion can be enhanced. The accuracy of detection of any void 20 in a TSV in processed detection images can be improved.

Subsequently, with reference to FIG. 5, a length of a TSV transmission image detected at the X-ray detector 5 when the X-ray detector 5 is inclined in the φ direction by the pivoting stage 6 is calculated. When it is assumed that the diameter of a TSV 11 formed in a wafer 2 is Φ and the height thereof is h and the length of a TSV transmission image acquired by applying an X-ray 200 from a direction inclined by φ is h', the following relational expression holds between these parameters:

[Ex. 1]

$$h' = h \cdot \sin\varphi + \Phi \cdot \cos\varphi \quad \text{(Ex. 1)}$$

Figure 6:
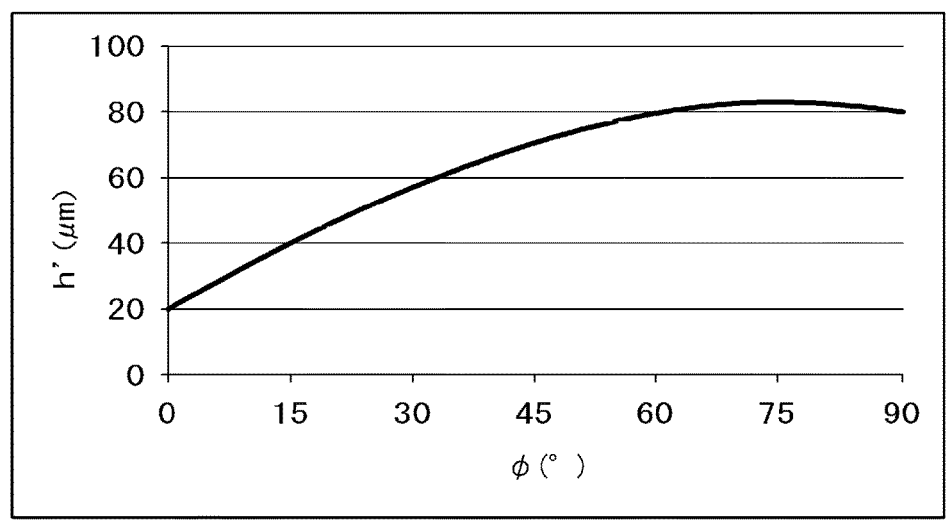
FIG. 6 is a drawing illustrating a relation between an inclination angle and a length of a TSV transmission image.

FIG. 6 shows a relation between an inclination angle φ and the length h' of a TSV transmission image determined by (Ex. 1). However, Φ=20 μm and h=80 μm. It was found that: within the range of 0<φ<75 degrees, h' was increased with increase in φ and at an angle larger than 75 degrees, h' was reduced. For example, when inclination φ=60 degrees, the length h' of the TSV transmission image is approximately 80 μm.

Figure 7:
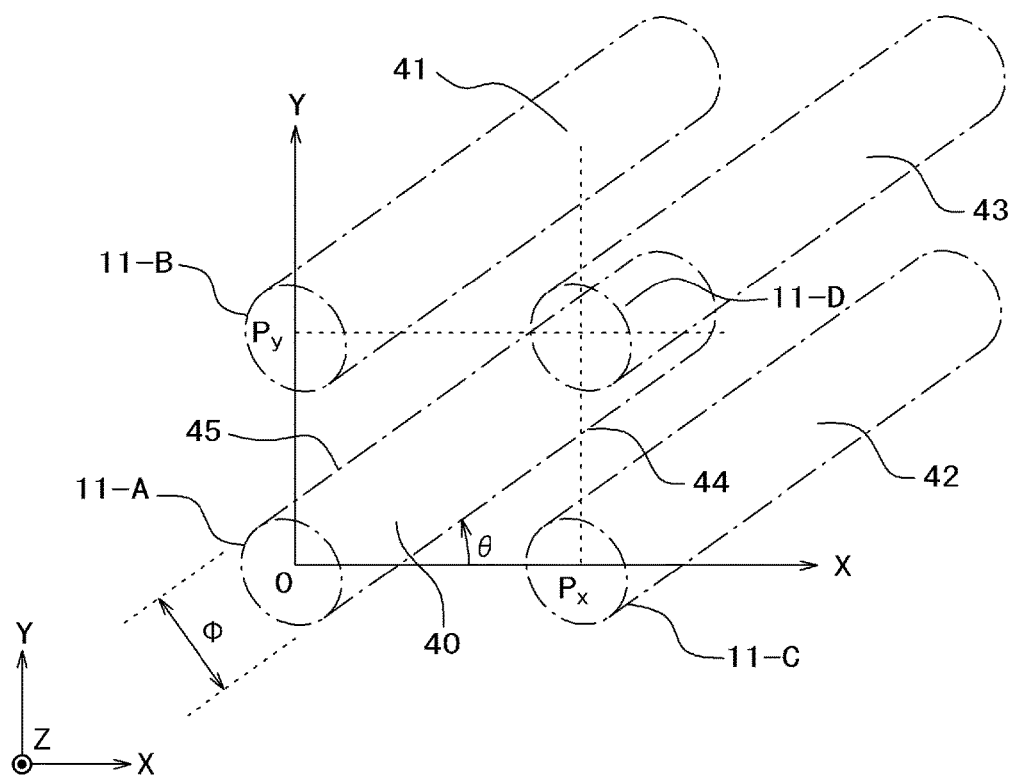
FIG. 7 is a drawing illustrating overlapping of TSV transmission images occurring when a wafer is rotated in a wafer in-plane direction.

A description will be given to a relation between an angle of rotation of a wafer 2 in the θ-direction within an XY-plane and overlapping of adjacent TSV transmission images with reference to FIG. 7. FIG. 7 shows an ideal relation between TSV transmission images and an angle of rotation in the θ-direction obtained when it is assumed that Φ=20 μm, h=80 μm, $P_x$=50 μm, $P_y$=40 μm and inclination angle φ=60 degrees.

In FIG. 7, four TSVs, TSVs 11-A, 11-B, 11-C, and 11-D are present and their respective TSV transmission images 40, 41, 42, and 43 have been detected at the X-ray detector 5. At this time, the center coordinates of TSV 11-A is set to (0,0), the center coordinates of TSV 11-B are set to (0,Py), the center coordinates of TSV 11-C are set to (Px,0), and the center coordinates of TSV 11-D are set to (Px,Py).

When attention is focused on the transmission image 40 of TSV 11-A, the respective transmission images do not overlap with each other by determining an angle of rotation θ such that the transmission image 40 passes between TSV 11-B and TSV 11-D or between TSV 11-C and TSV 11-D. When it is assumed that two straight lines in the longitudinal direction of the transmission image 40 are straight line 44 and straight line 45, these straight lines are respectively represented by (Ex. 2) and (Ex. 3) below:

[Ex. 2]

$$\text{Straight line 44: } Y_1 = a \cdot X_1 + b_1 \quad \text{(Ex. 2)}$$

[Ex. 3]

$$\text{Straight line 45: } Y_2 = a \cdot X_2 + b_2 \quad \text{(Ex. 3)}$$

where,

[Ex. 4]

$$a = \tan\theta \quad b_1 = 0.5\Phi \cdot \sin(\theta - 0.5\pi) - a \cdot \cos(\theta - 0.5\pi) \quad \text{(Ex. 4)}$$

[Ex. 5]

$$b_2 = 0.5\Phi \cdot \sin(\theta + 0.5\pi) - a \cdot \cos(\theta + 0.5\pi) \quad \text{(Ex. 5)}$$

Here, when θ satisfying Ex. 6 is obtained, the transmission image 40 passes between TSV 11-C and TSV 11-D and overlapping of transmission images can be eliminated:

[Ex. 6]

$$\frac{|aP_x + b_1|}{\sqrt{a^2+1}} > 0.5\Phi \text{ and } \frac{|aP_x - P_y + b_2|}{\sqrt{a^2+1}} > 0.5\Phi \quad \text{(Ex. 6)}$$

Similarly, when θ satisfying Ex. 7 is obtained, the transmission image 40 passes between TSV 11-B and TSV 11-D and overlapping of transmission images can be eliminated:

[Ex. 7]

$$\frac{|aP_x - P_y + b_1|}{\sqrt{a^2+1}} > 0.5\Phi \text{ and } \frac{|-P_y + b_2|}{\sqrt{a^2+1}} > 0.5\Phi \quad \text{(Ex. 7)}$$

Figure 8:
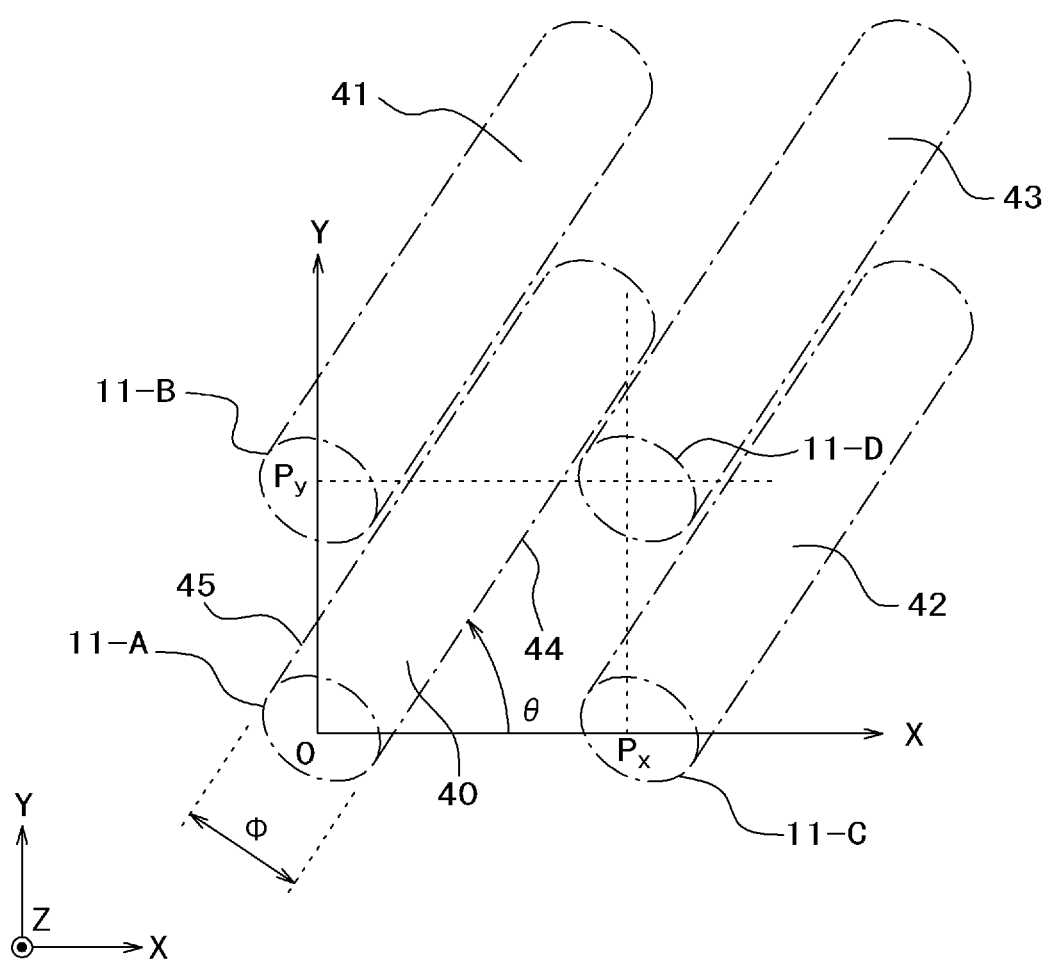
FIG. 8 illustrates an example of an X-ray detection image obtained without overlapping of transmission images.

In the case of the TSV shape and pitch in this example, θ satisfying (Ex. 6) is not present but (Ex. 7) is satisfied within the range of 61 degrees<θ<67 degrees. Hence, in the case of TSVs formed based on the above design information, X-ray transmission images in which overlapping of adjacent TSV transmission images is eliminated can be acquired by rotating the wafer 2 by an angle of 61 degrees to 67 degrees in the θ-direction as illustrated in FIG. 8.

In the description with reference to FIG. 7, TSV 11-A and TSV transmission image 40 are taken as an example. Since TSVs are formed in an identical shape with an identical pitch, overlapping of transmission images can be eliminated to pick up a transmission X-ray image also with respect to the other TSVs (11-B, 11-C, 11-D) by acquiring transmission images at the same angle of rotation.

FIG. 9A and FIG. 9B illustrate an example of GUI. The GUI screen embraces four sub-windows: an inspection mode window 110 for wafer inspection, a recipe creation window 111 for creating inspection recipes, a calibration window 112, and a load/unload window 113 for loading/unloading wafers.

In the calibration window 112 in FIG. 9A, it is possible to input such parameters as tube voltage and probe current and check an X-ray transmission image through a transmission image display window 50 in real time. A transmission image in any location can be observed by inputting appropriate coordinates. When the layout information of a wafer is known, the wafer layout information can be taken in from a pull-down menu 53. When an automatic angle of rotation calculation button 54 is pressed, an angle of rotation free from overlapping of transmission images is automatically calculated and that angle of rotation can be set. Needless to add, after automatic calculation, an angle of rotation may be manually inputted to adjust the angle of rotation.

A description has been given to a method of setting an angle of rotation with an ideal TSV transmission image assumed with reference to FIG. 7. In reality, there are also cases where TSVs are not formed in designed dimensions or with a designed pitch. In cases where an applied X-ray is not a parallel ray, a problem arises when the detector 5 is inclined relative to a wafer 2 by the pivoting stage 6 to acquire a transmission image. Since the wafer 2 and the detector 5 are not parallel to each other, in the acquired image, a difference in magnification is present in some location in the wafer 2. Therefore, even when an angle of rotation is calculated by the technique described in relation to this example, overlapping can occur. To cope with this, in this example, a transmission image is displayed in the transmission image display window 50 as illustrated in FIG. 9A so that the transmission image can be actually checked and an angle of rotation and an inclination angle can be finely adjusted from the set value display area 55.

In the transmission image display window 50, any straight line 51 can be drawn and a brightness profile 52 thereof can be displayed. A transmission image can be visually checked and in addition, overlapping of transmission images can be quantitively checked because a profile is displayed.

The recipe creation window 111 has functions of making settings for determining a wafer movement sequence and a brightness threshold value for defect determination, in addition to the parameters shown in the calibration window 112 and creating and storing recipes for wafer inspection (not shown). When inspection conditions set in accordance with conditions set in the calibration window 112 are appropriate, the conditions set in the calibration window 112 can be incorporated into the recipe creation window 111 to simplify recipe creation.

In the inspection mode window 110, it is possible to select a recipe created in the recipe creation window 111 and start or abort an inspection. It is also possible to store, read, and interpret inspection results (not shown).

In the load/unload window 113, it is possible to unload a wafer set in the X-ray inspection device 100 and load a wafer housed in a hoop (not shown).

Figure 10A:
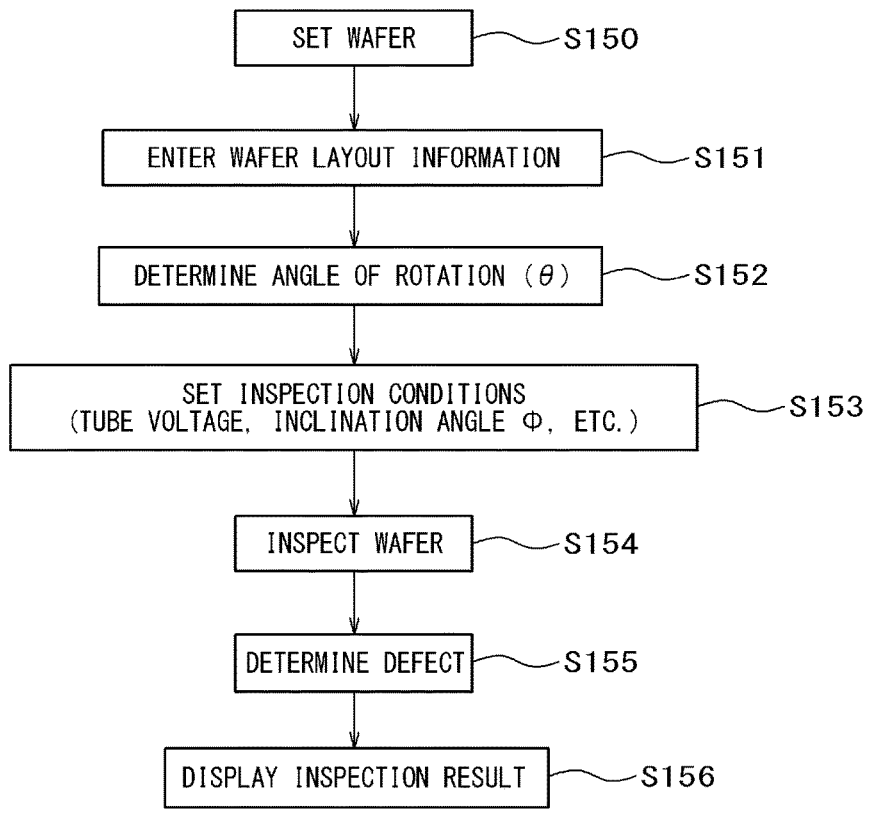
FIG. 10A is a flow diagram illustrating an inspection procedure in Example 1 of the present invention.

FIG. 10A illustrates an inspection flow according to this example.

S150: Set any wafer from a hoop set in the X-ray inspection device 100. A wafer may be manually set.

S151: Enter the layout information of the wafer. An angle of rotation is calculated from this layout information. An area where TSVs are present is extracted from the layout information and a wafer movement sequence is also set at the same time. Since the position of the X-ray source 1 is fixed, the relative position between the X-ray source 1 and the wafer 2 is changed when the wafer 2 is moved and the angle of rotation is also varied. Therefore, when a wafer transport sequence is set, the wafer is rotated by the rotating stage 4 as appropriate based on the coordinates of the translating stage 3 and such a wafer movement sequence that TSV transmission images do not overlap with each other is thereby set.

S152: Determine an angle of rotation. As mentioned above, there are cases where a result of automatic calculation and an optimal angle of rotation disagree with each other because of such a cause as a design error. In such a case, an optimal angle is checked and set again in the calibration screen.

S153: Input inspection conditions, such as tube voltage, tube current, and inclination angle.

S154: Inspect the wafer based on the conditions set at the steps up to S153 and acquire an X-ray transmission image.

S155: Perform a defect determination based on the acquired transmission image.

Figure 10B:
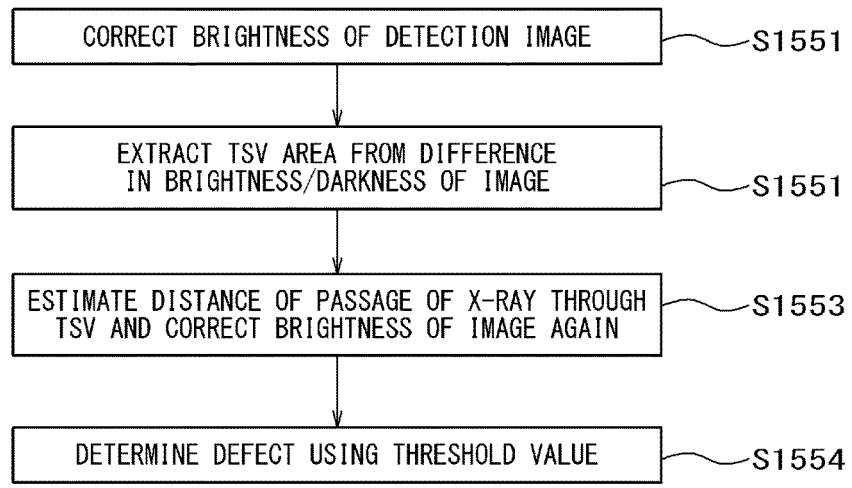
FIG. 10B is a flow diagram illustrating a defect determination procedure in Example 1 of the present invention.

FIG. 10B illustrates the processing flow of this step in detail. In a detection image, there is uneven brightness because of uneven brightness of the X-ray source 1 or uneven sensitivity from pixel to pixel of the X-ray detector 5. To cope with this, brightness correction is performed by shading correction (S1551). Since TSV areas are low in transmittance, a TSV area is subsequently extracted based on a difference in brightness/darkness of the image with corrected brightness (S1552). When it is assumed that each TSV is cylindrical, it is possible to estimate how far distance an X-ray incident upon each pixel has passed through a TSV (Cu) from the outline of the extracted TSV can be estimated. For this reason, brightness correction is performed again based thereon (S1553). Those involving a variation larger than a preset threshold value on the basis of variation in the brightness of the corrected transmission image are determined as a defect (S1554).

Figure 10C:
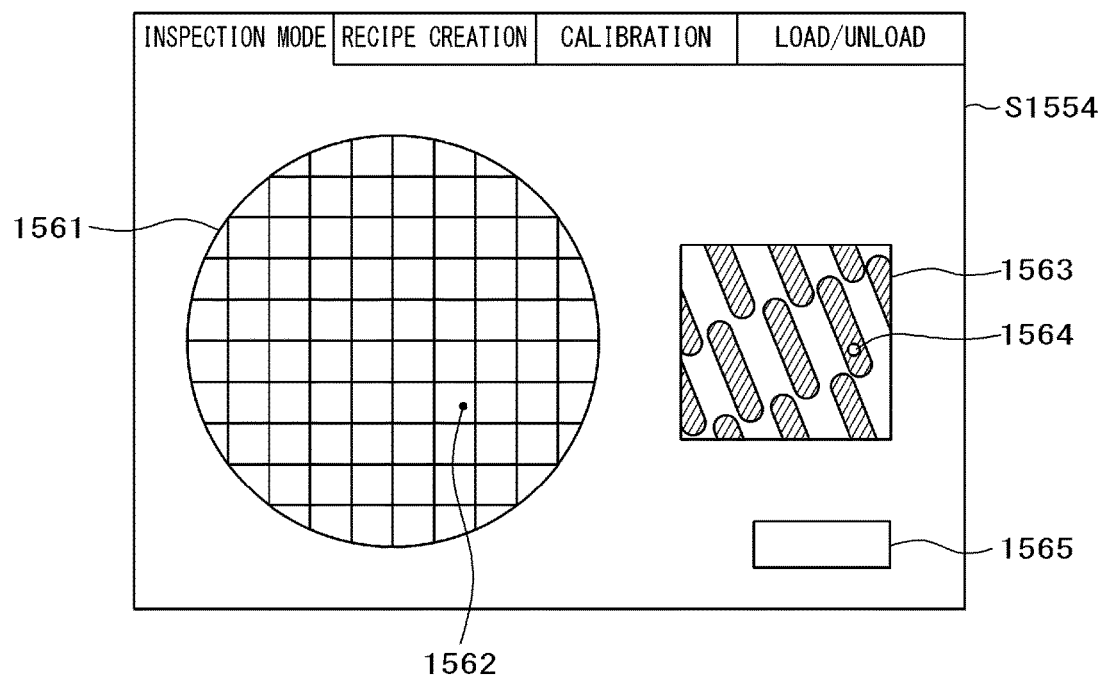
FIG. 10C is a front view of a screen displayed in an input/output unit in Example 1 of the present invention.

S156: Display an inspection result, such as the size and coordinates of a defect determined at S155, in the input/output unit 105. Required inspection results are stored in a recording medium, such as PC. FIG. 10C illustrates an example of a screen 1560 displayed in the input/output unit 105. A result indication button 1565 is displayed on the screen 1560. Clicking this result indication button 1565 on the screen displays a wafer overall view 1561 and the positional information of an area 1562 involving a detected defect is displayed thereon. Clicking the defect 1562 displayed in the wafer overall view 1561 with a pointer displays an enlarged image 1563 of the area 1562 involving the defect next to the wafer overall view 1561 and an enlarged image 1564 of a pattern involving the detected defect is displayed therein. Displaying an enlarged image of a pattern involving a defect enables the situation of occurrence of the defect to be visually grasped and can be utilized as a tool for early solving problems.

In the description of this example, a case where the target of the X-ray source 1 is a tungsten thin film and a diamond thin film is taken as an example but the present invention is not limited to this. Since the optimal energy of an X-ray differs depending on an object to be measured, the above configuration may be varied as appropriate with the properties, energy, and the like of the X-ray taken into account. The configuration of the electron optical system is not limited to the foregoing, either.

In the description of this example, a case where the X-ray detector 5 is an image intensifier obtained by combining a scintillator, a fluorescent material, and CCD is taken as an example but the present invention is not limited to this. For example, use of a flat panel display makes it possible to obtain a transmission image without distortion throughout the field of view and perform an inspection over a wide field of view.

In the description of this example, a case where a wafer 2 consists of three layers is taken as an example but the present invention is not limited to this. In the description of this embodiment, a case where each TSV is 20 µm in diameter and 80 µm in length and TSVs are formed with pitches of 40 µm and 50 µm is taken as an example but the present invention is not limited to this. Optimal angle of rotation and inclination angle can be set for each wafer based on design information.

In the description of this example, the GUI illustrated in FIG. 9 is taken as an example but the present invention is not limited to this. The description of a method for defect detection processing is described with reference to the flow 155 in FIG. 10 but the processing method is not limited to this.

In the description of a method for calculating an angle of rotation in this example, a case where TSVs are formed in a single pattern in an entire wafer is taken as an example but the present invention is not limited to this. For example, when TSVs are formed in a plurality of patterns in a wafer, an optimal angle of rotation can be set for each area where TSVs are formed in an identical pattern and when an inspection is performed, the angle of rotation can be varied from area to area.

In the description of this example, a case where TSVs are used as an object is taken as an example but the present invention is not limited to this. For example, since microbumps and Cu pillars are also regularly formed like TSVs, an optimal irradiation angle can be determined from information on the shape, depth, and pitch thereof. Structures, such as wiring and metal patterns, formed of metal have large atomic numbers; therefore, when the transmission images thereof overlap with each other, degradation in detection accuracy and erroneous detect can be incurred. Therefore, an angle of rotation may be set such that these structures do not overlap with each other.

In the description of this example, a case where the object to be measured is a wafer is taken as an example but the present invention is not limited to this. For example, the present invention is applicable to objects to be measured, for example, chips after dicing and MEMSs (Mechanical Electrical Micro Systems), in which a complicated pattern is formed.

In the description of this example, a case where an inclination angle φ is varied by moving the X-ray detector 5 is taken as an example but the present invention is not limited to this. For example, an inclination angle φ may be varied by rotating the opposite X-ray source 1 and X-ray detector 5 with a measuring point in a wafer 2 at the center while maintaining the positional relation therebetween. Alternatively, an inclination angle φ may be varied by inclining a wafer 2.

Figure 11:
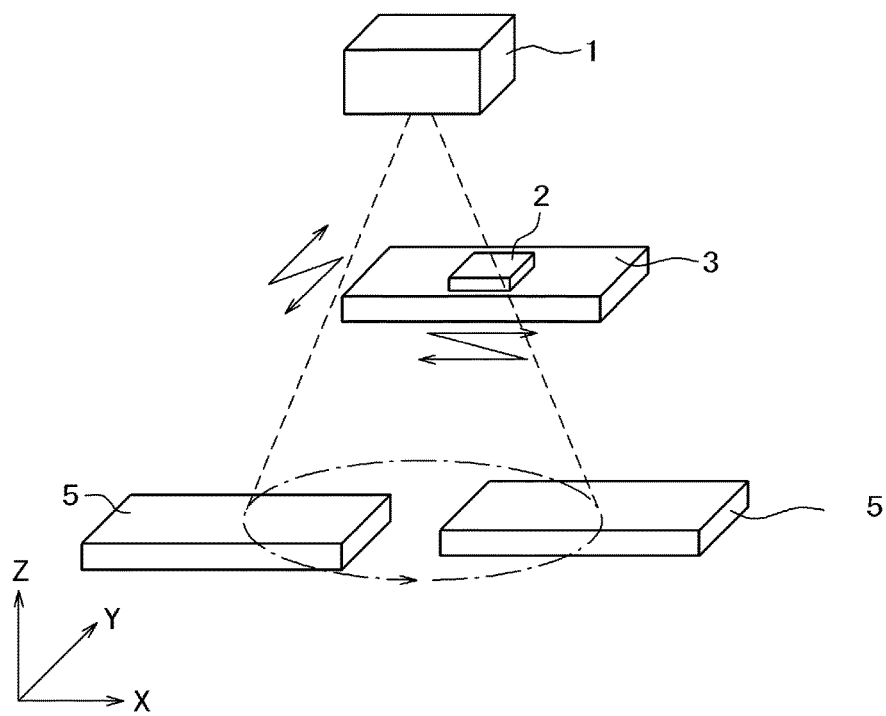
FIG. 11 is a drawing illustrating a device configuration used when an X-ray detector is rotated to vary an X-ray irradiation angle in Example 1 of the present invention.
Figure 12:
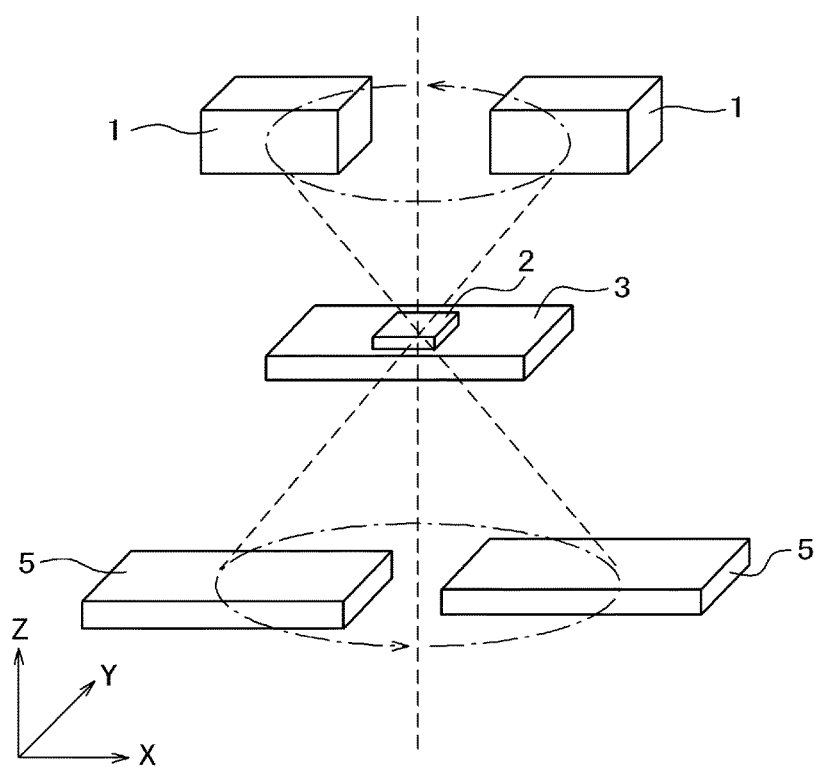
FIG. 12 is a drawing illustrating a device configuration used when an X-ray source and an X-ray detector are rotated to vary an X-ray irradiation angle in Example 1 of the present invention.

In the description of this example, a case where an X-ray irradiation angle is varied by rotating the rotating stage 4 is taken as an example but the present invention is not limited to this. For example, as illustrated in FIG. 11, an X-ray irradiation angle may be varied by rotating the X-ray detector 5 in the θ-direction within an XY-plane and accordingly translating the translating stage 3. As illustrated in FIG. 12, an X-ray irradiation angle may be varied by fixing the translating stage 3 and rotating the opposite X-ray source 1 and X-ray detector 5 in the θ-direction within an XY-plane with a measurement point in a wafer 2 at the center while maintaining the positional relation between the X-ray source 1 and the X-ray detector 5.

In the description of this example, a case where an inspection is performed with a plurality of Si chips laminated is taken as an example but the present invention is not limited to this. An inspection may be performed after each layer is laminated. Alternatively, an inspection may be performed after dicing and packaging.

Example 2

A schematic diagram of the X-ray inspection device 100 is the same as illustrated in FIG. 1. In the description of Example 1, a case where overlapping of adjacent TSV transmission images is prevented by optimizing an angle of rotation is taken as an example. However, there are cases where overlapping of transmission images inevitably occurs depending on a design layout. In such a case, an angle of rotation at which overlapping of transmission images is minimized can be set before an inspection.

Figure 13:
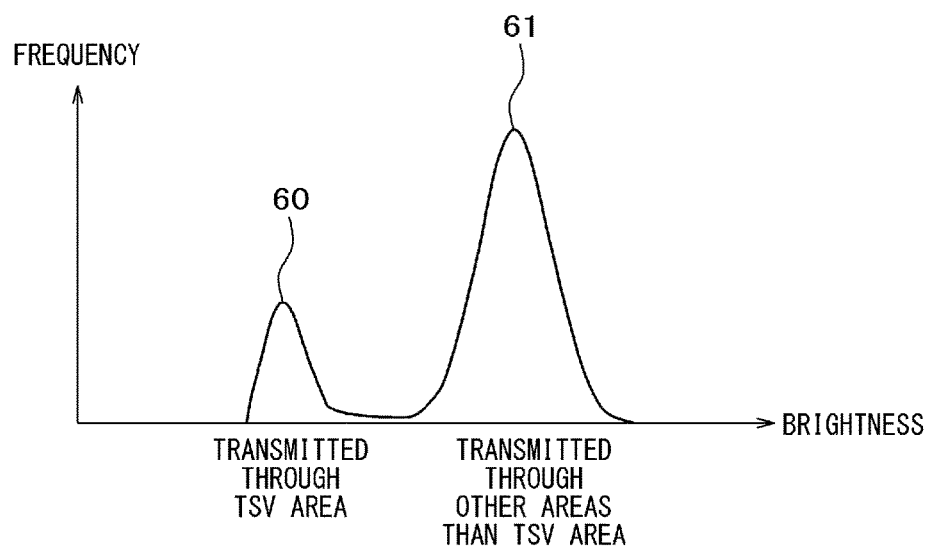
FIG. 13 illustrates an example of a histogram of the brightness of a transmission image.

When a histogram of a picked-up image free from overlapping of TSV transmission images as shown in FIG. 8 is generated, the histogram often has two peaks as shown in FIG. 13. Peak 60 is equivalent to the output of pixels that detected an X-ray transmitted through a TSV area and peak 61 is equivalent to the output of pixels that detected an X-ray transmitted through other areas than the TSV area.

Figure 14:
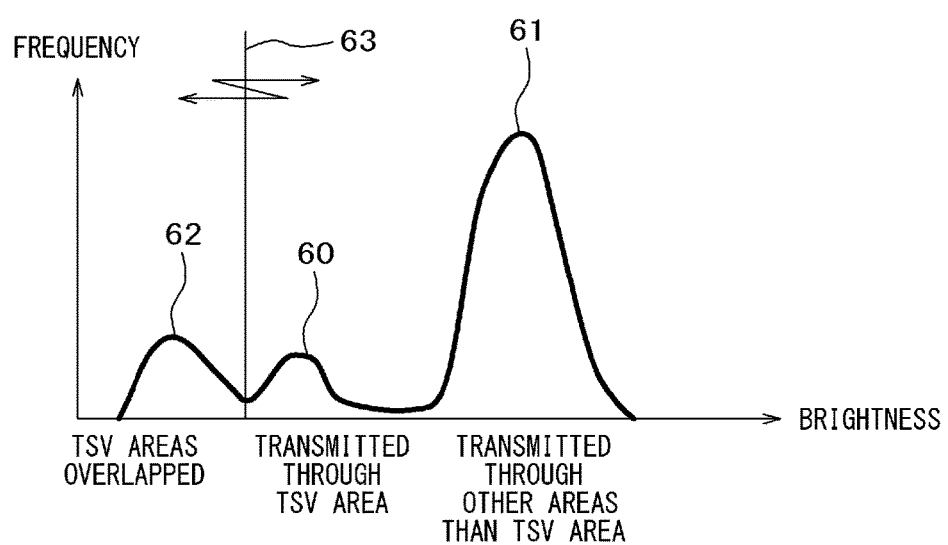
FIG. 14 illustrates an example of a histogram of the brightness of a transmission image.

When transmission images overlap with each other as shown in FIG. 7 and a histogram of a picked-up image thereof is generated, the histogram often has three peaks as shown in FIG. 14. Peak 62 is equivalent to the output of pixels that becomes darker than a single TSV transmission image because of overlapping of transmission images. An area where transmission images overlap with each other can be extracted by shifting threshold value 63 on this histogram and imaging only pixels equal to or lower than the threshold value. An angle at which overlapping of transmission images is minimized can be found by acquiring transmission images while varying an angle of rotation and performing the threshold value processing on the histogram of each picked-up image.

Figure 15:
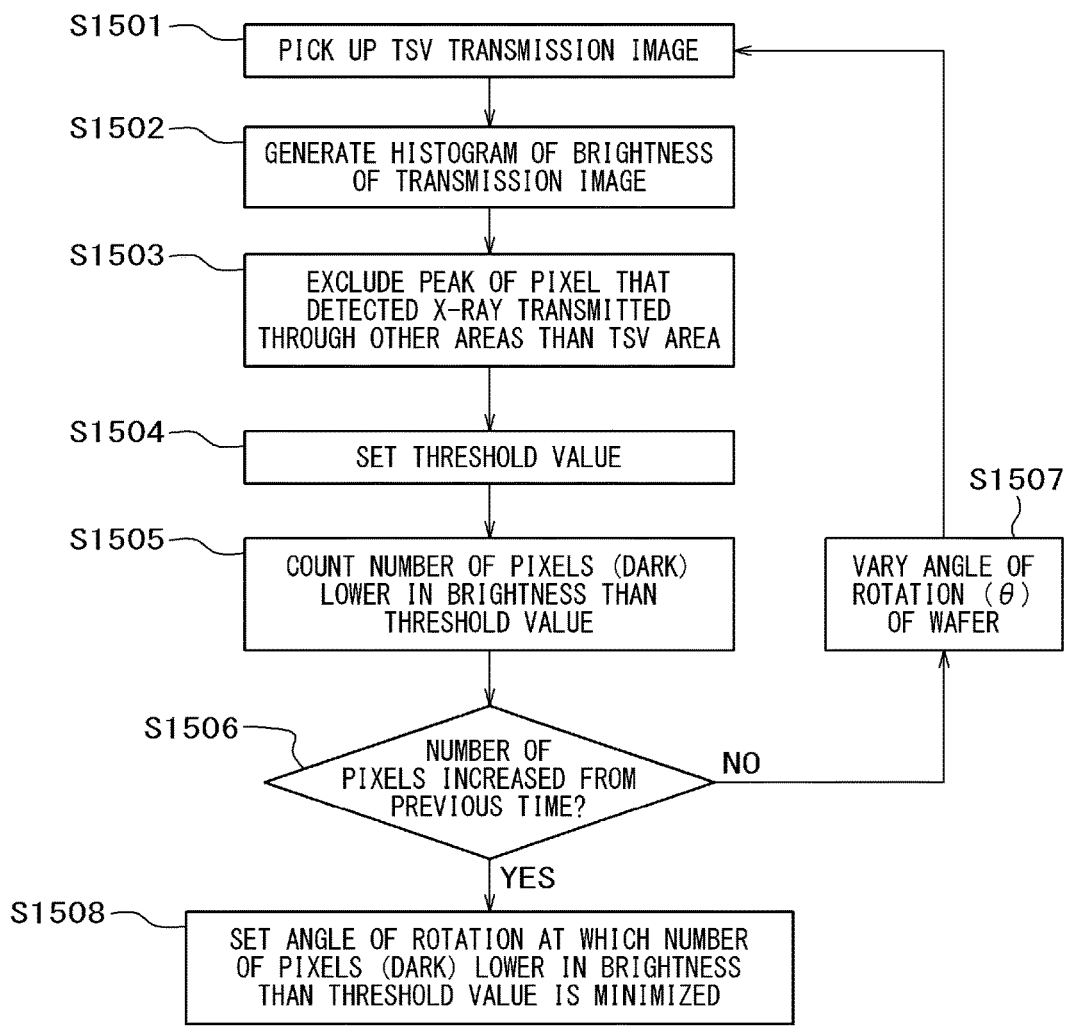
FIG. 15 is a flow diagram illustrating a procedure for processing to determine an angle of rotation θ of a wafer 2 at which overlapping of transmission images is minimized in Example 2 of the present invention.

FIG. 15 illustrates a procedure of processing for determining an angle of rotation θ of a wafer 2 at which overlapping of transmission images is minimized. An angle of rotation is determined by the following procedure:

S1501: Pick up a transmission image of an area where a TSV is present.

S1502: Generate a histogram of the brightness of each pixel from the transmission image.

S1503: Visually exclude peak 61 equivalent to the output of pixels that detected an X-ray transmitted through other areas than the TSV area. Alternatively, set a fixed threshold value in advance and exclude peak 61.

S1504: Set threshold value 63. At this time, the threshold value 63 may be manually set or may be automatically set.

In case of automatic setting, a discriminating identification method, a mode method, a Kittler method, or the like can be used.

S1505: Count the number of pixels whose brightness is lower than the threshold value 63.

S1506: Check whether the number of pixels whose brightness lower than the threshold value 63 counted this time has been increased from the number of pixels previously counted.

S1507: When the number of pixels has not been increased, vary the angle of rotation (θ) of the wafer 2 and repeat the processing of S1501 to S1506.

S1508: When the check at S1506 reveals that the number of pixels has been increased, set an angle of rotation at which the number of pixels whose brightness is lower than the threshold value 63 is at the minimum as an angle of rotation (θ) of the wafer 2 at which overlapping of transmission images is minimized.

At S1506, it may be checked whether increase in the number of pixels whose brightness is lower than the threshold value 63 from the number of pixels previously counted has been repeated by a predetermined number of times.

When the threshold value 63 is manually set, the magnitude thereof may be fixed or may be varied from image to image.

When the three peaks are not obviously separated as shown in FIG. 14 and a threshold value cannot be automatically discriminated, a threshold value can be manually set for every image. Alternatively, a fixed threshold value may be set in advance and processing may be automatically performed.

When the three peaks cannot be obviously separated as shown in FIG. 14, the tube voltage or the tube current may be adjusted such that the peaks can be easily separated. At this time, inspection conditions need not be identical with those for inspection.

When overlapping of transmission images is automatically discriminated, erroneous setting of an angle of rotation can be avoided by displaying an inspection result on GUI such that a user can visually check it.

In the description of this example, a case where an angle of rotation is set based on the number of pixels whose brightness is lower than the threshold value 63 is taken as an example but the present invention is not limited to this. For example, a total sum of the brightness of pixels whose brightness is equal to or lower than the threshold value 63 may be calculated and an angle of rotation may be set based thereon.

Example 3

A schematic diagram of the X-ray inspection device 100 is the same as illustrated in FIG. 1. In the description of Example 1, a case where an X-ray is obliquely applied and an inspection is performed without overlapping of transmission images is taken as an example; in the description of Example 2, a case where an angle of rotation of a wafer 2 is set to an angle of rotation at which overlapping of transmission images is minimized before inspection. In this example, an inspection may be under such conditions that adjacent TSV transmission images do not overlap with each other by reducing an inclination angle (φ) of the X-ray detector 5.

When it is assumed that Φ=20 μm, PX=50 μm, and Py=40 μm in FIG. 7, the angle formed between a diagonal line connecting the center of TSV 11-A and the center of TSV 11-D and the X-axis is 38.7 degrees and the distance between the two TSVs is 44 μm. As a result, when the length of transmission images is not more than 54 μm (=distance 44 μm between TSVs+radius 10 μm of TSVs), they do not overlap with each other. It will be assumed that the length h of TSVs is 80 μm. When an inclination angle (φ) of the X-ray detector 5 is set to 25 degrees in this case, the length of transmission images is approximately 51 μm and it is understood that overlapping of transmission images does not occur.

As described with reference to FIG. 4, the contrast of transmission images is increased by increasing an inclination angle (φ) of the X-ray detector 5 and this makes it easier to detect any void in TSVs. Even when an inclination angle is small, an inspection may be performed with an inclination angle reduced as mentioned above as long as a high S/N is obtained.

Example 4

Figure 16:
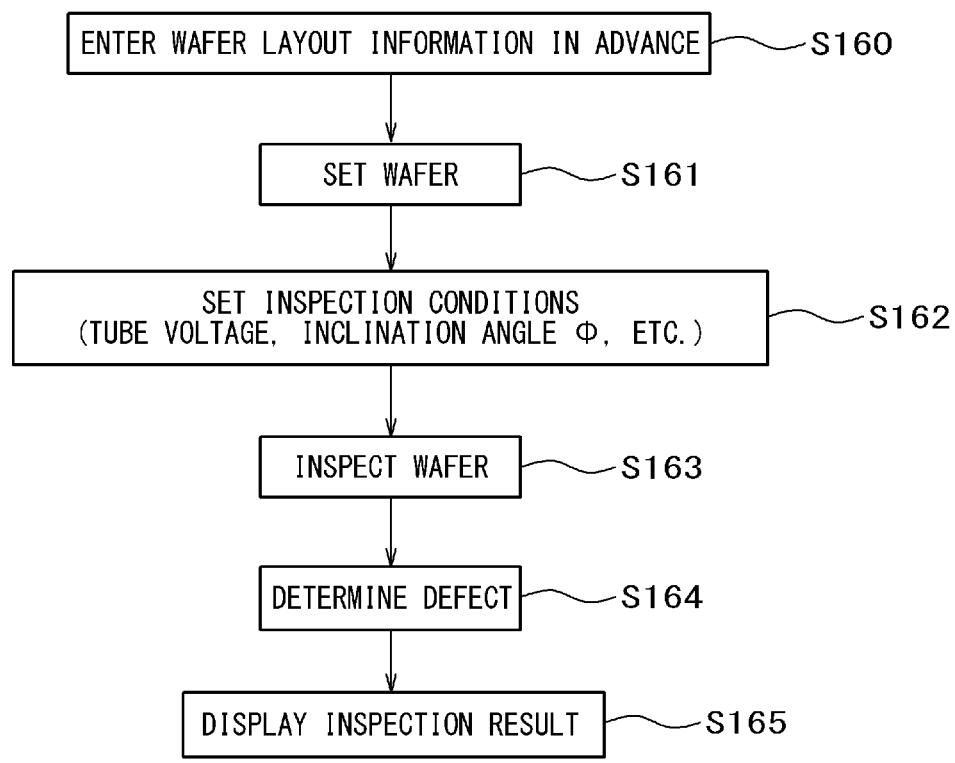
FIG. 16 is an explanatory diagram of an inspection flow taken when a recipe is established before a wafer is set.

A schematic diagram of the X-ray inspection device 100 is the same as illustrated in FIG. 1. In the description of Example 1, a case where after a wafer is set, the layout information of the wafer 2 is inputted to set an angle of rotation of the wafer 2 is taken as an example. When layout information has been already known when a wafer 2 is set, an angle of rotation of the wafer 2 can be automatically calculated. FIG. 16 illustrates an inspection flow therefor.

S160: Enter the layout information of a wafer to be inspected. An angle of rotation is calculated from this layout information. When the shape or arrangement of TSVs differs from location to location in a wafer, an angle of rotation at which transmission images do not overlap with each other is set for each location to create a basic recipe before the wafer is set. A wafer movement sequence is also set at this time. Since the position of the X-ray source 1 is fixed, the relative position between the X-ray source 1 and the wafer 2 is varied and an angle of rotation is also changed when the wafer 2 is moved. Therefore, when a wafer transport sequence is set, the wafer is rotated by the rotating stage 4 as appropriate based on the coordinates of the translating stage 3 and such a wafer movement sequence that overlapping of TSV transmission images does not occur is set.

S161: Set a wafer whose layout information has been entered at flow 160 from a hoop set in the X-ray inspection device 100. Alternatively, the wafer may be manually set.

The processing of S162 to S165 is the same as the processing of S153 to S156 described with reference to FIG. 10.

In this example, a recipe can be created without use of a true wafer. For example, when an arrangement interval of TSVs is large and it is apparent from a theoretical calculation that overlapping of TSV transmission images will not occur, a time required to create a recipe can be shortened by implementing this example to inspect the wafer.

Example 5

Figure 17:
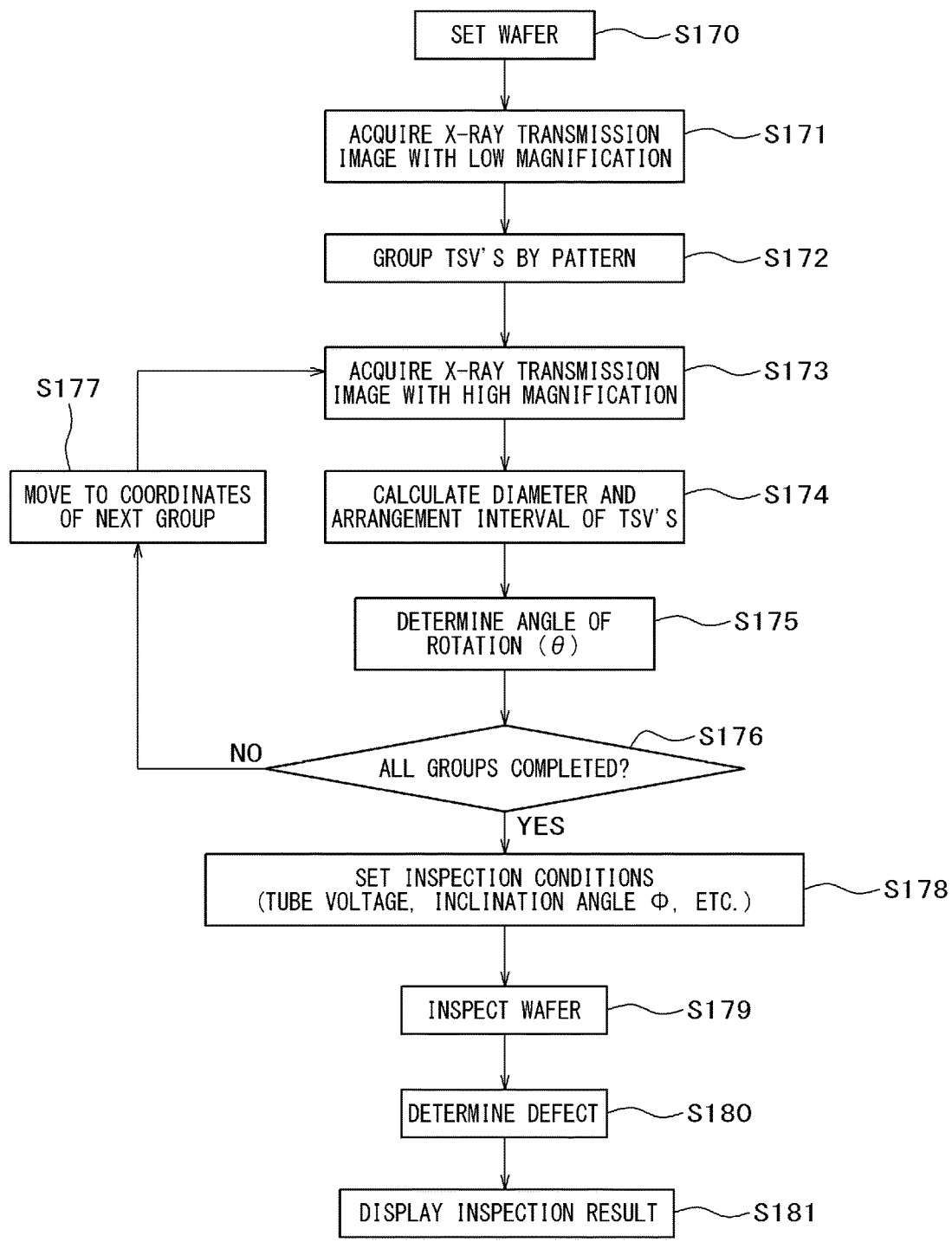
FIG. 17 is an explanatory diagram of an inspection flow taken when a recipe of a wafer with unknown layout information is established.

A schematic diagram of the X-ray inspection device 100 is the same as illustrated in FIG. 1. In the description of Example 1, a case where the layout information of a wafer 2 is known is taken as an example. Even when wafer layout information is unknown, an angle of rotation at which overlapping of transmission images does not occur or is minimized can be set from transmission images acquired before recipe creation. FIG. 17 illustrates an inspection flow therefor.

S170: Set any wafer from a hoop set in the X-ray inspection device 100. A wafer may be manually set.

S171: Acquire an X-ray transmission image with a low magnification in order to measure the layout of the entire wafer. At this time, an X-ray is applied from the perpendicular direction of the wafer to acquire a transmission image. To acquire a plurality of transmission images, the transmission images can be acquired such that there is an area where images overlap with each other in each image and then the images can be integrated.

S172: Extract areas where a TSV is present from the overall layout acquired at S171, calculate areas where similar patterns are formed according to the diameter and arrangement interval of TSVs, and group the TSVs by pattern. To extract TSVs, for example, the following technique can be used. Threshold value processing is performed on a transmission image and a binary image is calculated. Since TSVs are cylindrical, circular areas are extracted from the binary image and the diameter and center coordinates thereof are calculated to obtain a diameter and an arrangement interval.

S173: First, move the stage such that TSVs in a first group come into the field of view. Set an X-ray irradiation angle to the perpendicular direction of the wafer and acquire a transmission image with a higher magnification than that in flow 170. The magnification can be set such that at least four (2×2) TSVs are included.

S174: Calculate the diameter and arrangement interval (in the X-axis direction and the Y-axis direction) of TSVs from the image acquired at S173.

S175: Calculate an angle of rotation using the technique described in relation to Example 1 or Example 2.

S176: If setting of an angle of rotation is completed with respect to all the groups classified at S172, proceed to S178. If the setting has not been completed, proceed to S177.

S177: Move the stages such that the TSVs in a group for which an angle of rotation has not been set yet come into the field of view and repeat the processing of S173 to S175.

S178: Input inspection conditions such as tube voltage, tube current, inclination angle, and the like. In addition, set a movement sequence for the wafer under inspection.

The processing of S179 to S181 is the same as the processing of S154 to S156 described with reference to FIG. 10.

Figure 18:
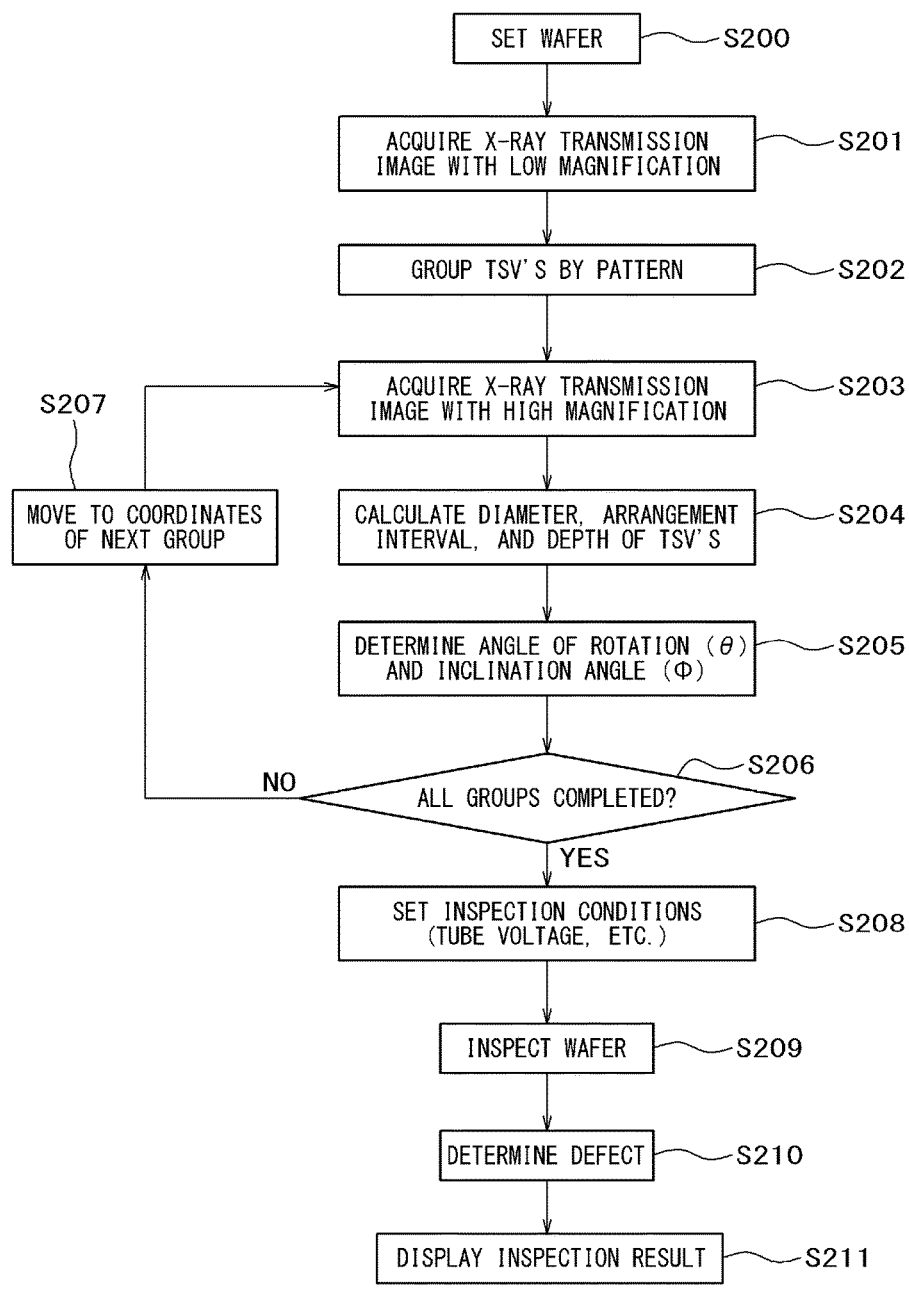
FIG. 18 is an explanatory diagram of an inspection flow taken when a recipe of a wafer with unknown layout information is established.

In the description of the above example, a case where an X-ray is applied only from the perpendicular direction of a wafer is taken as an example. In addition to the perpendicular direction, an X-ray may also be obliquely applied and a recipe may be created based on these two transmission images. FIG. 18 illustrates an inspection flow therefor.

S200: Same as S150 described with reference to FIG. 10.
S201: Same as S170 described with reference to FIG. 17.
S202: Same as S171 described with reference to FIG. 17.
S203: First, move the stage such that TSVs in a first group come into the field of view. Set an X-ray irradiation angle to the perpendicular direction of the wafer and acquire a transmission image with a higher magnification than that in flow 170. The magnification can be set such that at least four (2×2) TSVs are included. Obliquely apply an X-ray and acquire a second transmission image under the condition that the same TSVs should be embraced in the field of view.

S204: Calculate the diameter, arrangement interval (in the X-axis direction and the Y-axis direction), and depth of TSVs from the two images acquired at S203.

S205: Calculate an angle of rotation and an inclination angle using the techniques described in relation to Example 1 to Example 3.

S206: If setting of an angle of rotation and an inclination angle is completed with respect to all the groups classified at S202, proceed to S208. If the setting has not been completed, proceed to S207.

S207: Move the stage such that the TSVs in a group for which an angle of rotation and an inclination angle have not been set yet come into the field of view and repeat the processing of S203 to S205.

S208: Input inspection conditions such as tube voltage, tube current, and the like. In addition, set a movement sequence for the wafer under inspection.

The processing of S209 to S211 is the same as the processing of S154 to S156 described with reference to FIG. 10.

In the description of Example 1 to Example 4, cases where an angle of rotation and an inclination angle are set with the layout information of a wafer known is taken as an example. According to this example, a recipe can be created even when the layout information of a wafer is unknown.

Up to this point, a concrete description has been given to the invention made by the present inventors based on embodiments. However, the present invention is not limited to these embodiments and may be variously modified without departing from the subject matter thereof, needless to add.

INDUSTRIAL APPLICABILITY

The present invention is applicable to an X-ray inspection device configured to inspect a semiconductor device in process using an X-ray at some midpoint in a process of manufacturing the semiconductor device.

REFERENCE SIGNS LIST

1 . . . X-ray source,
2 . . . Wafer,
3 . . . Translating stage,
4 . . . Rotating stage,
5 . . . X-ray detector,
6 . . . Pivoting stage,
7 . . . X-ray shielding wall,
10 . . . Die,
11, 11-A, 11-B, 11-C, 11-D . . . TSV,
12 . . . Microbump,
13 . . . First layer,
14 . . . Second layer,
15 . . . Third layer,
20 . . . Void,
40 to 43 . . . TSV transmission image,
54 . . . Automatic angle of rotation calculation button,
100 . . . X-ray inspection device,
101 . . . X-ray source controller,
102 . . . Stage controller,
103 . . . X-ray detector controller,
104 . . . Control unit,
105 . . . Input/output unit,
200 . . . X-ray.

The invention claimed is:

1. An X-ray inspection method comprising the steps of:
applying an X-ray emitted from an X-ray source to a sample to be inspected placed on a rotating stage and having structures formed in the sample to be inspected;
detecting an X-ray transmitted through the sample irradiated with the X-ray with an X-ray detector;
processing a signal, obtained by detecting an X-ray transmitted through the sample with the X-ray detector, to form an X-ray transmission image at an image processing unit; and
processing the X-ray transmission image formed at the image processing unit to detect any defect in the sample at a defect determination unit,
wherein detection of an X-ray transmitted through the sample at the X-ray detector is performed by: determining a detection azimuth relative to the sample of an X-ray transmitted through the sample, detected with the X-ray detector and a detection elevation angle relative to the X-ray source based on information on the arrangement interval, depth, and planar shape of structures formed in the sample; adjusting an angle of rotation of a rotating stage on which the sample is placed according to the determined detection azimuth; and setting the position of the detector to the determined detection elevation angle and detecting an X-ray transmitted through the sample.

2. The X-ray inspection method according to claim 1, wherein a detection elevation angle of an X-ray transmitted through the sample, detected with the X-ray detector relative to the X-ray source is determined as an angle relative to a position in which the X-ray source emits the X-ray.

3. The X-ray inspection method according to claim 1, wherein a detection azimuth relative to the sample and a detection elevation angle relative to the X-ray source are determined such that overlapping of the X-ray transmission images of the structures does not occur.

4. The X-ray inspection method according to claim 1, wherein a detection azimuth relative to the sample and a detection elevation angle relative to the X-ray source are determined such that overlapping of the X-ray transmission images of structures formed in the sample is minimized.

5. The X-ray inspection method according to claim 4, wherein an amount of overlapping of structures formed in the sample is calculated from an X-ray transmission image formed at the image processing unit.

6. The X-ray inspection method according to claim 1, wherein the sample is a silicon (Si) substrate and the structures are a repetitively formed pattern of metal.

7. The X-ray inspection method according to claim 1, wherein information on the determined detection azimuth relative to the sample and detection elevation angle relative to the X-ray source are displayed on a screen.

8. An X-ray inspection method comprising the steps of:
applying an X-ray emitted from an X-ray source to a sample to be inspected placed on a rotating stage and having structures formed in the sample to be inspected;
detecting an X-ray transmitted through the sample irradiated with an X-ray with an X-ray detector;
processing a signal, obtained by detecting an X-ray transmitted through the sample detected with the X-ray detector to from an X-ray transmission image at an image processing unit; and
processing the X-ray transmission image formed at the image processing unit to detect any defect in the sample at a defect determination unit,
wherein the X-ray transmission image formed by processing a signal, obtained by detecting an X-ray transmitted through the sample detected with the X-ray detector, at an image processing unit is displayed on a screen; and
a detection azimuth of an X-ray transmitted through the sample detected with the X-ray detector relative to the sample and a detection elevation angle relative to the X-ray source are determined such that overlapping of the X-ray transmission images of the structures formed in the sample does not occur on the screen displaying the X-ray transmission images or such that overlapping of the X-ray transmission images of the structures is minimized.

9. The X-ray inspection method according to claim 8, wherein the sample is a silicon (Si) substrate and the structures are a repetitively formed pattern of metal.

10. The X-ray inspection method according to claim 8, wherein information on the determined detection azimuth relative to the sample and detection elevation angle relative to the X-ray source is displayed on a screen.

11. An X-ray inspection device comprising:
a rotating stage on which a sample to be inspected can be placed and which is rotatable within a plane;
an X-ray source applying an X-ray to a sample placed on the rotating stage;
an X-ray detector detecting an X-ray emitted from the X-ray source and transmitted through the sample;
a pivoting stage adjusting an elevation angle of the X-ray detector relative to a position in which the X-ray source emits the X-ray;
an image processing unit processing a signal obtained by detecting an X-ray transmitted through the sample, detected at the X-ray detector to form an X-ray transmission image;
a defect determination unit processing the X-ray transmission image, formed at the image processing unit, at the defect determination unit to detect any defect in the sample; and
a control unit controlling the rotating stage and the pivoting stage,
wherein the control unit controls an angle of rotation of a rotating stage on which the sample is placed based on information on the arrangement interval, depth, and planar shape of structures formed in the sample or the X-ray transmission image formed at the image processing unit, thereby setting a detection azimuth of the X-ray detector relative to the sample and controls a pivoting angle of the pivoting stage relative to a position in which the X-ray source emits an X-ray, thereby setting a detection elevation angle of the X-ray detector relative to the X-ray source.

12. The X-ray inspection device according to claim 11, wherein the control unit determines the detection azimuth and the detection elevation angle such that overlapping of the X-ray transmission images of the structures does not occur.

13. The X-ray inspection device according to claim 11, wherein the control unit determines a detection azimuth of the X-ray detector relative to the sample and a detection elevation angle relative to the X-ray source such that overlapping of the X-ray transmission images of the structures is minimized.

14. The X-ray inspection device according to claim 13, wherein the control unit calculates an amount of overlapping of the structures from an X-ray transmission image formed at the image processing unit.

15. The X-ray inspection device according to claim 11, further comprising:
a screen displaying information on the determined detection azimuth and detection elevation angle.

* * * * *